US012426851B2

(12) United States Patent
Hu et al.

(10) Patent No.: US 12,426,851 B2
(45) Date of Patent: Sep. 30, 2025

(54) METHOD, SYSTEM, APPARATUS AND MEDIUM FOR MONITORING ABDOMINAL RESPIRATION BASED ON ULTRASOUND IMAGE

(71) Applicant: THE SECOND AFFILIATED HOSPITAL OF GUANGZHOU MEDICAL UNIVERSITY, Guangzhou (CN)

(72) Inventors: Nan Hu, Guangzhou (CN); Fengshan Huang, Guangzhou (CN); Shihao Hu, Guangzhou (CN); Mingfu Ye, Guangzhou (CN)

(73) Assignee: THE SECOND AFFILIATED HOSPITAL OF GUANGZHOU MEDICAL UNIVERSITY, Guangzhou (CN)

( * ) Notice: Subject to any disclaimer, the term of this patent is extended or adjusted under 35 U.S.C. 154(b) by 0 days.

(21) Appl. No.: 19/007,919

(22) Filed: Jan. 2, 2025

(65) Prior Publication Data
US 2025/0281151 A1 Sep. 11, 2025

Related U.S. Application Data

(63) Continuation of application No. PCT/CN2024/116194, filed on Sep. 2, 2024.

(30) Foreign Application Priority Data

Mar. 11, 2024 (CN) .......................... 202410273532.6

(51) Int. Cl.
A61B 8/08 (2006.01)
A61B 8/00 (2006.01)

(52) U.S. Cl.
CPC .......... A61B 8/0858 (2013.01); A61B 8/5223 (2013.01)

(58) Field of Classification Search
CPC ........................... A61B 8/0858; A61B 8/5223
See application file for complete search history.

(56) References Cited

U.S. PATENT DOCUMENTS

| 2012/0016254 A1 | 1/2012 | Masuo |
| 2021/0128117 A1* | 5/2021 | Iseri .......................... A61B 8/14 |

(Continued)

FOREIGN PATENT DOCUMENTS

| CN | 109289118 A | 2/2019 |
| CN | 114983469 A | 9/2022 |
| EP | 4176796 A1 | 10/2023 |

OTHER PUBLICATIONS

Title of the Item: Medicina 2021 Publication Date: Sep. 2, 2022 Name of the Author: Jung Won Kwon et al. Article Title: Breathing Exercise Called the Maximal Abdominal Contraction Maneuver pp. 1-7.

*Primary Examiner* — Bo Joseph Peng
(74) *Attorney, Agent, or Firm* — Nitin Kaushik

(57) ABSTRACT

Disclosed are a method, system, apparatus and storage medium for monitoring abdominal breathing based on ultrasound image, comprising, an abdominal ultrasound image of user at the end of calm expiration and during the abdominal respiration is acquired; according to the abdominal ultrasound image, the corresponding external abdominal oblique muscle, internal abdominal oblique muscle and transversus abdominis muscle is recognized; the thickness of the external abdominal oblique muscle, internal abdominal oblique muscle and transversus abdominis muscle is calculated; the external abdominal oblique muscle recruitment intensity, internal abdominal oblique muscle recruitment intensity, transversus abdominis muscle recruitment intensity is cal- (Continued)

culated according to the thickness of external abdominal oblique muscle, internal abdominal oblique muscle and transversus abdominis muscle; the external abdominal oblique muscle recruitment intensity, the internal abdominal oblique muscle recruitment intensity and the transversus abdominis muscle recruitment intensity is compared with a corresponding preset target value, and a monitoring result is obtained.

6 Claims, 9 Drawing Sheets

(56) References Cited

U.S. PATENT DOCUMENTS

| | | | |
|---|---|---|---|
| 2023/0414889 A1* | 12/2023 | Haartsen | A61B 8/5292 |
| 2023/0419527 A1* | 12/2023 | Hendriks | A61B 8/0858 |
| 2024/0091474 A1* | 3/2024 | Hendriks | A61M 16/0051 |
| 2024/0277254 A1* | 8/2024 | Haartsen | A61B 8/5223 |

* cited by examiner

METHOD, SYSTEM, APPARATUS AND MEDIUM FOR MONITORING ABDOMINAL RESPIRATION BASED ON ULTRASOUND IMAGE

CROSS-REFERENCE TO RELATED APPLICATIONS

The application claims priority to Chinese patent application No. 2024102735326, filed on Mar. 11, 2024, the entire contents of which are incorporated herein by reference.

TECHNICAL FIELD

The present invention belongs to the technical field of image processing and specifically relates to a method, system, apparatus and medium for monitoring abdominal respiration based on ultrasound image.

BACKGROUND

Abdominal respiration is the best exercise mode for exercising human respiratory function and activating inner core muscles. A high-quality abdominal respiration requires the participation of deep abdominal muscle. How to monitor the activity of deep abdominal muscle non-invasively and in real time, effectively activate deep abdominal muscle is a key to ensure high-quality abdominal respiration. The ultrasound image obtained by musculoskeletal ultrasound can reflect muscle thickness, thereby reflecting muscle contraction ability and can be used as a non-invasive muscle function assessment method.

However, the existing ultrasound monitoring method usually requires doctor to hold the ultrasound probe, and guide user to breathe throughout the process. And the monitoring image used for abdominal respiration training is all professional ultrasound image, and the training must be completed under the full supervision of medical care; the labor cost is higher. And the calculation method of muscle recruitment intensity needs to be manually measured by a professional doctor; the operation is complicated, and user is difficult to self-test.

SUMMARY

An object of the present invention is to provide a method, system, apparatus and medium for monitoring abdominal respiration based on ultrasound image, which can realize real-time monitoring of abdominal respiration and facilitate the self-monitoring of the training of abdominal respiration.

The first aspect of the present invention provides a method for monitoring abdominal respiration based on ultrasound image, comprising:

A first abdominal ultrasound image of user at the end of quiet expiration and a plurality of second abdominal ultrasound images under abdominal respiration condition is acquired;

Image recognition is performed on the first abdominal ultrasound image, and the first external abdominal oblique muscle, the first internal abdominal oblique muscle and the first transversus abdominis muscle is recognized. Image recognition is performed on each of the second abdominal ultrasound image, and the second external abdominal oblique muscle, the second internal abdominal oblique muscle and the second transversus abdominis muscle is recognized;

The thickness of the first external abdominal oblique muscle, the first internal abdominal oblique muscle, the first transversus abdominis muscle, the second external abdominal oblique muscle, the second internal abdominal oblique muscle and the second transversus abdominis muscle is calculated, and the first external abdominal oblique muscle thickness, the first internal abdominal oblique muscle thickness, the first transversus abdominis muscle thickness, the second external abdominal oblique muscle thickness, the second internal abdominal oblique muscle thickness and the second transversus abdominis muscle thickness is obtained;

The external abdominal oblique muscle recruitment intensity is calculated according to the first external oblique muscle thickness and the second external abdominal oblique muscle thickness; the internal abdominal oblique muscle recruitment intensity is calculated according to the first internal abdominal oblique muscle thickness and the second internal abdominal oblique muscle thickness; the transversus abdominis muscle recruitment intensity is calculated according to the first transversus abdominis muscle thickness and the second transversus abdominis muscle thickness;

The external abdominal oblique muscle recruitment intensity, the internal abdominal oblique muscle recruitment intensity and the transversus abdominis muscle recruitment intensity, which are corresponding to each of the second abdominal ultrasound image is compared with a corresponding preset target value, and a monitoring result is obtained.

In some of these embodiments, image recognition is performed on the first abdominal ultrasound image, and the first external abdominal oblique muscle, the first internal abdominal oblique muscle and the first transversus abdominis muscle is recognized, comprising:

The first abdominal ultrasound image is preprocessed, and a first preprocessed image is obtained;

According to the pixel value of the first preprocessed image, the first fascia of quiet expiration, the second fascia of quiet expiration, the third fascia of quiet expiration and the fourth fascia of quiet expiration which are sequentially arranged is recognized. The abdominal muscle between the first fascia of quiet expiration and the second fascia of quiet expiration is the first external abdominal oblique muscle; the abdominal muscle between the second fascia of quiet expiration and the third fascia of quiet expiration is the first internal abdominal oblique muscle; the abdominal muscle between the third fascia of quiet expiration and the fourth fascia of quiet expiration is the first transversus abdominis muscle.

In some of these embodiments, the thickness of the first external abdominal oblique muscle, the first internal abdominal oblique muscle and the first transversus abdominis muscle is calculated, and the first external abdominal oblique muscle thickness, the first internal abdominal oblique muscle thickness and the first transversus abdominis muscle thickness is obtained, comprising:

Aline segment corresponding to the first fascia of quiet expiration, the second fascia of quiet expiration, the third fascia of quiet expiration and the fourth fascia of quiet expiration is constructed;

The line segment corresponding to the first fascia of quiet expiration, the second fascia of quiet expiration, the third fascia of quiet expiration and the fourth fascia of quiet expiration is split into a plurality of sub-line segments;

The points with the maximum and minimum slope in each sub-line segment, which are corresponding to the first fascia of quiet expiration, the second fascia of quiet expiration, the third fascia of quiet expiration and the fourth fascia of quiet expiration are selected as key points;

The key point on the second fascia of quiet expiration, which has the shortest absolute distance from each key point on the first fascia of quiet expiration is selected, and a corresponding first key point pair is formed. The average value of the distance of the first key point pair is calculated, and the first external abdominal oblique muscle thickness is obtained;

The key point on the third fascia of quiet expiration, which has the shortest absolute distance from each key point on the second fascia of quiet expiration is selected, and a corresponding second key point pair is formed. The average value of the distance of the second key point pair is calculated, and the first internal abdominal oblique muscle thickness is obtained;

The key point on the fourth fascia of quiet expiration, which has the shortest absolute distance from each key points on the third fascia of quiet expiration is selected, and a corresponding third key point pair is formed. The average value of the distance of the third key point pair is calculated, and the first transversus abdominis muscle thickness is obtained.

In some of these embodiments, image recognition is performed on each of the second abdominal ultrasound image, and the second external abdominal oblique muscle, the second internal abdominal oblique muscle and the second transversus abdominis muscle is recognized, comprising:

The second abdominal ultrasound image is preprocessed, and a second preprocessed image is obtained;

According to the pixel value of the second preprocessed image, the first fascia of abdominal respiration, the second fascia of abdominal respiration, the third fascia of abdominal respiration and the fourth fascia of abdominal respiration which are sequentially arranged is recognized. The abdominal muscle between the first fascia of abdominal respiration and the second fascia of abdominal respiration is the second external abdominal oblique muscle; the abdominal muscle between the second fascia of abdominal respiration and the third fascia of abdominal respiration is the second internal abdominal oblique muscle; the abdominal muscle between the third fascia of abdominal respiration and the fourth fascia of abdominal respiration is the second transversus abdominis muscle.

In some of these embodiments, the thickness of the second external abdominal oblique muscle, the second internal abdominal oblique muscle and the second transversus abdominis muscle is calculated, and the second external abdominal oblique muscle thickness, the second internal abdominal oblique muscle thickness and the second transversus abdominis muscle thickness is obtained, comprising:

A line segment model corresponding to the first fascia of abdominal respiration, the second fascia of abdominal respiration, the third fascia of abdominal respiration and the fourth fascia of abdominal respiration is constructed, and a corresponding line segment is obtained;

The line segment corresponding to the first fascia of abdominal respiration, the second fascia of abdominal respiration, the third fascia of abdominal respiration and the fourth fascia of abdominal respiration is split into a plurality of sub-line segments;

The points with the maximum and minimum slope in each of the sub-line segment, which are corresponding to the first fascia of abdominal respiration, the second fascia of abdominal respiration, the third fascia of abdominal respiration and the fourth fascia of abdominal respiration are selected as key points;

The key point on the second fascia of abdominal respiration, which has the shortest absolute distance from each key point on the first fascia of abdominal respiration is selected, and a corresponding fourth key point pair is formed. The average value of the distance of the fourth key point pair is calculated, and the second external abdominal oblique muscle thickness is obtained;

The key point on the third fascia of abdominal respiration, which has the shortest absolute distance from each key point on the second fascia of abdominal respiration is selected, and a corresponding fifth key point pair is formed. The average value of the distance of the fifth key point pair is calculated, and the second internal oblique muscle thickness is obtained;

The key point on the fourth fascia of abdominal respiration, which has the shortest absolute distance from each key point on the third fascia of abdominal respiration is selected, and a corresponding sixth key point pair is formed. The average value of the distance of the sixth key point pair is calculated, and the second transversus abdominis muscle thickness is obtained.

In some of these embodiments, the external abdominal oblique muscle recruitment intensity is calculated according to the first external abdominal oblique muscle thickness and the second external abdominal oblique muscle thickness; the internal abdominal oblique muscle recruitment intensity is calculated according to the first internal abdominal oblique muscle thickness and the second internal abdominal oblique muscle thickness; the transversus abdominis muscle recruitment intensity is calculated according to the first transversus abdominis muscle thickness and the second transversus abdominis muscle thickness, comprising:

The external abdominal oblique muscle recruitment intensity, the internal abdominal oblique muscle recruitment intensity and the transversus abdominis muscle recruitment intensity is calculated by adopting the recruitment intensity calculation formula, wherein the recruitment intensity calculation formula is as follows:

$$Q = \frac{h_2 - h_1}{h_1},$$

Wherein the Q denotes the recruitment intensity, the $h_2$ denotes the muscle thickness at the end of abdominal respiration and the $h_1$ denotes the muscle thickness at the end of quiet expiration;

The first external abdominal oblique muscle thickness is taken as $h_1$ and the second external abdominal oblique muscle thickness is taken as $h_2$; the $h_1$ and the $h_2$ is substituted into the recruitment intensity calculation formula, and the external abdominal oblique muscle recruitment intensity is obtained. The first internal abdominal oblique muscle thickness is taken as $h_1$ and the second internal abdominal oblique muscle thickness is taken as $h_2$; the $h_1$ and the $h_2$ is substituted into the recruitment intensity calculation formula, and the internal abdominal oblique muscle recruitment intensity is obtained. The first transversus abdominis muscle thickness is taken as $h_1$ and the second transversus abdominis muscle thickness is taken as $h_2$; the $h_1$ and the $h_2$ is substituted into the recruitment intensity calculation formula, and the transversus abdominis muscle recruitment intensity is obtained.

The second aspect of the present invention provides a system for monitoring abdominal respiration based on ultrasound image, comprising:

An ultrasound image acquisition module is used for acquiring user's first abdominal ultrasound image at the end of quiet expiration and a plurality of second abdominal ultrasound images under abdominal respiration condition;

An abdominal muscle recognition module is used for performing image recognition on the first abdominal ultrasound image, and the first external abdominal oblique muscle, the first internal abdominal oblique muscle and the first transversus abdominis muscle is recognized. Image recognition is performed on each of the second abdominal ultrasound image, and the second external abdominal oblique muscle, the second internal abdominal oblique muscle and the second transversus abdominis muscle is recognized;

An abdominal muscle thickness calculation module is used for calculating the thicknesses of the first external abdominal oblique muscle, the first internal abdominal oblique muscle, the first transversus abdominis muscle, the second external abdominal oblique muscle, the second internal abdominal oblique muscle and the second transversus abdominis muscle, and the first external abdominal oblique muscle thickness, the first internal abdominal oblique muscle thickness, the first transversus abdominis muscle thickness, the second external abdominal oblique muscle thickness, the second internal abdominal oblique muscle thickness and the second transversus abdominis muscle thickness is obtained;

A recruitment intensity calculation module is used for calculating the external abdominal oblique muscle recruitment intensity according to the first external abdominal oblique muscle thickness and the second external abdominal oblique muscle thickness. The internal abdominal oblique muscle recruitment intensity is calculated according to the first internal abdominal oblique muscle thickness and the second internal abdominal oblique muscle thickness. The transversus abdominis muscle recruitment intensity is calculated according to the first transversus abdominis muscle thickness and the second transversus abdominis muscle thickness;

A comparison module is used for comparing the external abdominal oblique muscle recruitment intensity, the internal abdominal oblique muscle recruitment intensity and the transversus abdominis muscle recruitment intensity which are corresponding to each of the second abdominal ultrasound image with a corresponding preset target value, and a monitoring result is obtained.

In some of these embodiments, the abdominal muscle recognition module, comprising:

A preprocessing unit is used for preprocessing the first abdominal ultrasound image, and the first preprocessed image is obtained;

A recognition unit is used for recognizing the first fascia of quiet expiration, the second fascia of quiet expiration, the third fascia of quiet expiration and the fourth fascia of quiet expiration which are sequentially arranged according to the pixel value of the first preprocessed image. The abdominal muscle between the first fascia of quiet expiration and the second fascia of quiet expiration is the first external abdominal oblique muscle; the abdominal muscle between the second fascia of quiet expiration and the third fascia of quiet expiration is the first internal abdominal oblique muscle; the abdominal muscle between the third fascia of the quiet expiration and the fourth fascia of the quiet expiration is the first transversus abdominis muscle.

The third aspect of the present invention provides a computer equipment, comprising a memory and a processor. The memory stores a computer program. The processor implements the steps of the method when the computer program is executed.

The fourth aspect of the present invention provides a computer-readable storage medium, storing a computer program thereon. When the computer program is executed by a processor, the step of the method is implemented.

The technical solution provided by the present invention has the following advantage and effect: by acquiring a first abdominal ultrasound image and a plurality of second abdominal ultrasound images, a monitoring of abdominal respiration in real time is realized. The abdominal muscle thickness and the recruitment intensity is calculated; and the recruitment intensity is compared with a preset target value, and a monitoring result is obtained, so that user can self-monitor the training of abdominal respiration and meet user's home-based rehabilitation needs.

DESCRIPTION OF REFERENCE NUMERALS

100—the first fascia of quiet expiration; 200—the second fascia of quiet expiration; 300—the third fascia of quiet expiration; 400—the fourth fascia of quiet expiration; 500—the first fascia of abdominal respiration; 600—the second fascia of abdominal respiration; 700—the third fascia of abdominal respiration; 800—the fourth fascia of abdominal respiration.

DETAILED DESCRIPTION OF THE EMBODIMENTS

For ease of understanding of the present invention, exemplary embodiments of the present invention will be described in more detail in the following text with reference to the attached drawings in the present invention.

Unless specifically stated or otherwise defined, the term used herein "first, second . . . " is only for the purpose of distinguishing name and does not represent a specific number or sequence.

Unless specifically stated or otherwise defined, the term used herein "and/or" includes any and all combinations of one or more of the associated listed items.

It needs to be stated that "fixed to" and "connected to" in the present invention can be directly fixed or connected to a component and also can be indirectly fixed or connected to a component.

Figure 1:
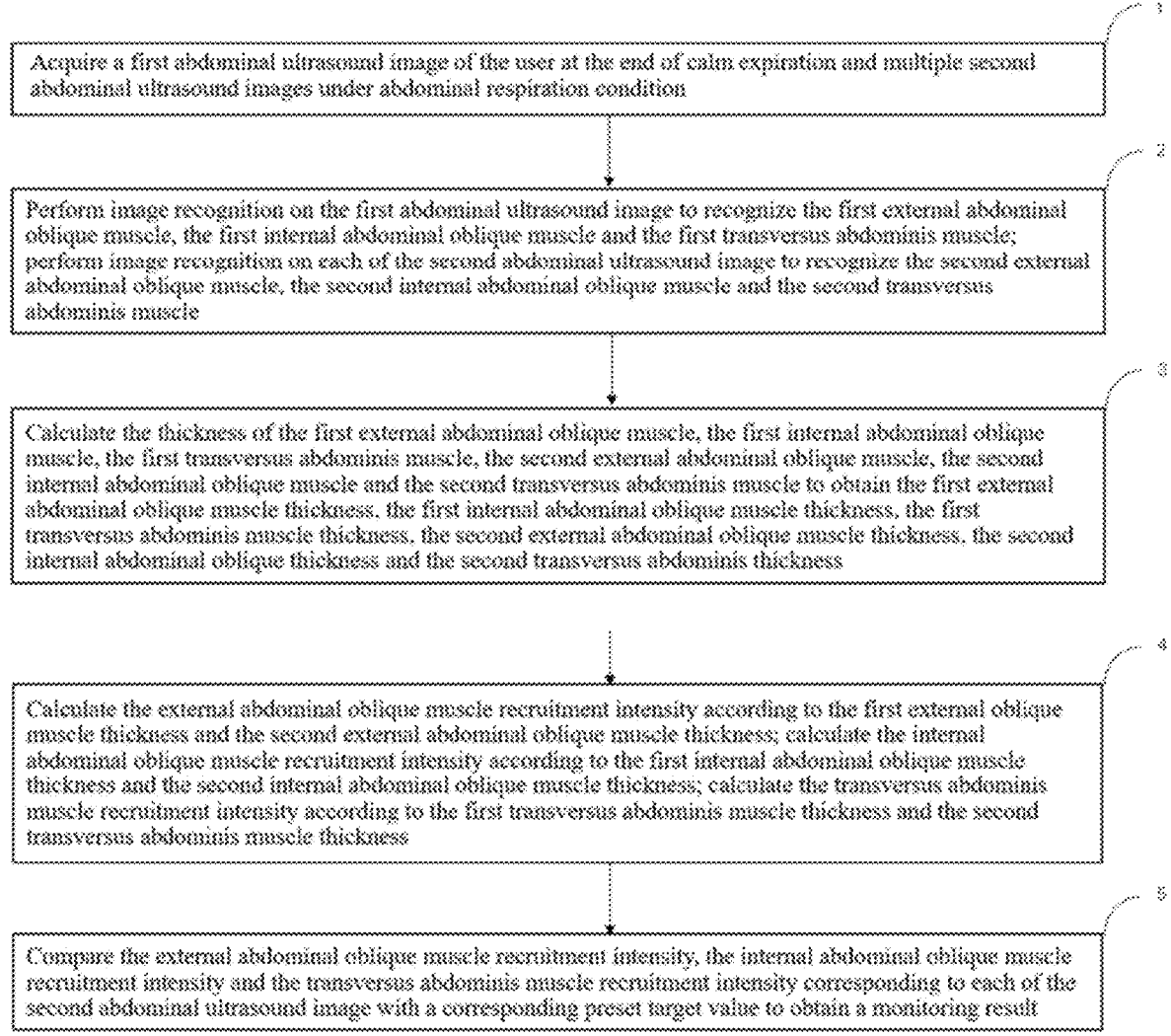
FIG. 1 is a flow diagram illustrating a method for monitoring abdominal respiration based on ultrasound image provided in the present invention.

As shown in FIG. 1, the embodiment of the present invention provides a method for monitoring abdominal respiration based on an ultrasound image, comprising:

Step 1: a first abdominal ultrasound image of user at the end of quiet expiration and a plurality of second abdominal ultrasound images under abdominal respiration condition is acquired.

In practical application, user can hold a wireless ultrasound probe and perform abdominal muscle measurement. The wireless ultrasound probe and the terminal are connected via Bluetooth. The terminal can be a mobile terminal, such as a mobile phone, a tablet computer, etc.

Specifically, when user is at the end of a quiet expiration, a wireless ultrasound probe is used to acquire abdominal ultrasound image, and a first abdominal ultrasound image is obtained. The abdominal ultrasound image of user is continuously acquired during abdominal respiration of user, and a plurality of second abdominal ultrasound images are obtained. When the abdominal ultrasound image is collected by using the wireless ultrasound probe, the wireless ultrasound probe is placed at the intersection of the anterior axillary line and the umbilical line, and the wireless ultrasound probe is parallel to the anterior axillary line. During measurement, the wireless ultrasound probe can move slightly at the intersection with the rise and fall of the respiration to ensure that the collected abdominal ultrasound image can collect the external abdominal oblique muscle, internal abdominal oblique muscle and transversus abdominis muscle, and keep the fascia of each abdominal muscle layer parallel to each other as much as possible. Meanwhile, a sufficient coupling needs to be smeared, leaving no space between the wireless ultrasound probe and the skin, and the wireless ultrasound probe should be gently tightly attached to the skin, and the abdominal muscle cannot be squeezed excessively to cause the abdominal muscle to be flattened.

Step 2: image recognition is performed on the first abdominal ultrasound image, and the first external abdominal oblique muscle, the first internal abdominal oblique muscle and the first transversus abdominis muscle is recognized. Image recognition is performed on each of the second abdominal ultrasound image, and the second external abdominal oblique muscle, the second internal abdominal oblique muscle and the second transversus abdominis muscle is recognized.

Specifically, image recognition is performed on the first abdominal ultrasound image, and the first external abdominal oblique muscle, the first internal abdominal oblique muscle and the first transversus abdominis muscle is recognized, comprising:

The first abdominal ultrasound image is preprocessed, and a first preprocessed image is obtained;

According to the pixel value of the first preprocessed image, the first fascia of quiet expiration, the second fascia of quiet expiration, the third fascia of quiet expiration and the fourth fascia of quiet expiration which are sequentially arranged is recognized. The abdominal muscle between the first fascia of quiet expiration and the second fascia of quiet expiration is the first external abdominal oblique muscle; the abdominal muscle between the second fascia of quiet expiration and the third fascia of quiet expiration is the first internal abdominal oblique muscle; the abdominal muscle between the third fascia of quiet expiration and the fourth fascia of quiet expiration is the first transversus abdominis muscle.

Figure 2:
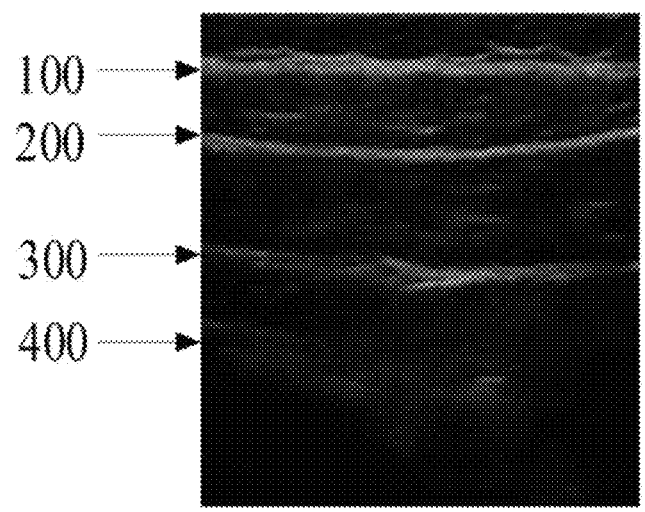
FIG. 2 is a diagram illustrating a first abdominal ultrasound image of user at the end of quiet expiration provided by the present invention.

In practical application, the first abdominal ultrasound image is preprocessed, comprising: the first abdominal ultrasound image is processed to be grayscale and normalization, and a first preprocessed image is obtained; the pixel value of the first preprocessed image is the gray value of the first preprocessed image. In the present embodiment, the pixel points with the pixel value greater than a first preset threshold in the first preprocessed image are recorded as the first fascial points, and a plurality of first fascial regions are obtained. Connecting the adjacent first fascial regions that are spaced within a preset spacing, and a first connected region, a second connected region, a third connected region and a fourth connected region which are sequentially arranged are obtained. An average pixel value of the first connected region, the second connected region, the third connected region and the fourth connected region is calculated. The connected area with the average pixel value greater than the second preset threshold is taken as the first fascia of quiet expiration. As shown in FIG. 2, if the first connected region is the first fascia of quiet expiration 100, then the second connected region is the second fascia of quiet expiration 200, the third connected region is the third fascia of quiet expiration 300, the fourth connected region is the fourth fascia of quiet expiration 400; if the fourth connected region is the first fascia of quiet expiration, then the third connected region is the second fascia of quiet expiration, the second connected region is the third fascia of quiet expiration, the first connected region area is the fourth fascia of quiet expiration. According to the knowledge of physiology, the abdominal muscle between the first fascia of quiet expiration and the second fascia of quiet expiration is taken as the first external abdominal oblique muscle; the abdominal muscle between the second fascia of quiet expiration and the third fascia of quiet expiration is the first internal abdominal oblique muscle; the abdominal muscle between the third fascia of quiet expiration and the fourth fascia of quiet expiration is taken as the first transversus abdominis muscle. In other embodiment, an abdominal muscle recognition model can be established based on deep learning. The first preprocessed image is input into the model, and the first external abdominal oblique muscle, the first internal abdominal oblique muscle and the first transversus abdominis muscle is recognized.

Specifically, image recognition is performed on each of the second abdominal ultrasound image, and the second external abdominal oblique muscle, the second internal abdominal oblique muscle and the second transversus abdominis muscle is recognized, comprising:

The second abdominal ultrasound image is preprocessed, a second preprocessed image is obtained;

According to the pixel value of the second preprocessed image, the first fascia of abdominal respiration, the second fascia of abdominal respiration, the third fascia of abdominal respiration and the fourth fascia of abdominal respiration, which are sequentially arranged is recognized. The abdominal muscle between the first fascia of abdominal respiration and the second fascia of abdominal respiration is the second external abdominal oblique muscle; the abdominal muscle between the second fascia of abdominal respiration and the third fascia of abdominal respiration is the second internal abdominal oblique muscle; the abdominal muscle between the third fascia of abdominal respiration and the fourth fascia of abdominal respiration is the second transversus abdominis muscle.

Figure 5:
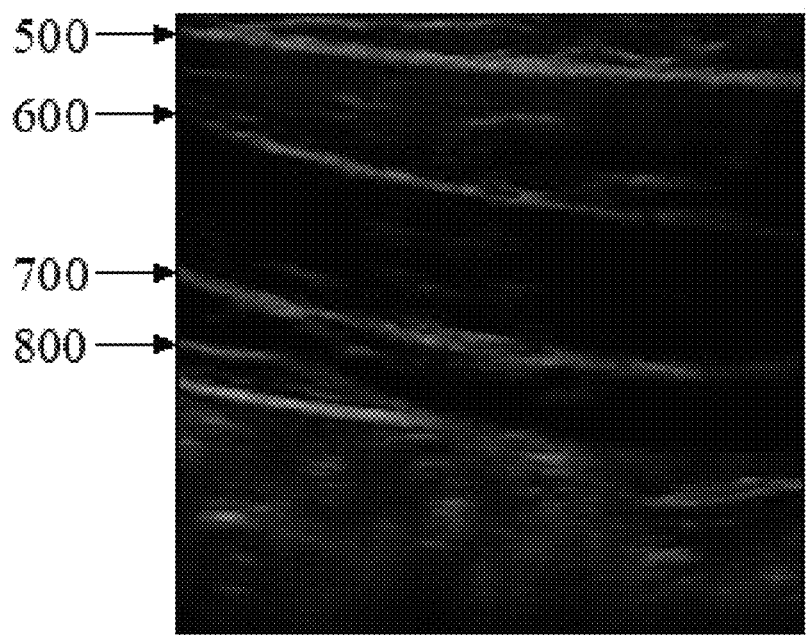
FIG. 5 is a diagram illustrating a second abdominal ultrasound image of user during abdominal expiration provided by the present invention.

In practical application, the preprocessing of the second abdominal ultrasound image is the same as the preprocessing of the first abdominal ultrasound image; the second abdominal ultrasound image is also processed to be grayscale and normalization, and a second preprocessed image is obtained. The second preprocessed image is processed in the same way as the first preprocessed image, and the second external abdominal oblique muscle, the second internal abdominal oblique muscle and the second transversus abdominis muscle is recognized. Specifically, the pixel points with the pixel value greater than a first preset threshold in the second preprocessed image are recorded as the second fascial points, and a plurality of second fascial regions are obtained. Connecting the adjacent second fascial regions that are spaced within a preset spacing, and the fifth connected region, the sixth connected region, the seventh connected region and the eighth connected region which are sequentially arranged are obtained. The average pixel values of the fifth connected region, the sixth connected region, the seventh connected region and the eighth connected region is calculated. The connected region with the average pixel value greater than the second preset threshold is taken as the first fascia of abdominal respiration. As shown in FIG. 5, if the fifth connected region is the first fascia of abdominal respiration 500, then the sixth connected area is the second fascia of abdominal respiration 600, the seventh connected area is the third fascia of abdominal respiration 700, and the eighth connected area is the fourth fascia of abdominal respiration 800; if the eighth connected area is the first fascia of abdominal respiration, then the seventh connected area is the second fascia of abdominal respiration, the sixth connected area is the third fascia of abdominal respiration, and the fifth connected area is the fourth fascia of abdominal respiration. According to the knowledge of physiology, the abdominal muscle between the first fascia of abdominal respiration and the second fascia of abdominal respiration is taken as the second external abdominal oblique muscle; the abdominal muscle between the second fascia of abdominal respiration and the third fascia of abdominal respiration is taken as the second internal abdominal oblique muscle; the abdominal muscle between the third fascia of abdominal respiration and the fourth fascia of abdominal respiration is taken as the second transversus abdominis muscle. Similarly, an abdominal muscle recognition model can also be established based on deep learning. The second preprocessed image is input into the model, and the second external abdominal oblique muscle, the second internal abdominal oblique muscle and the second transversus abdominis muscle is recognized.

Step 3: the thicknesses of the first external abdominal oblique muscle, the first internal abdominal oblique muscle, the first transversus abdominis muscle, the second external abdominal oblique muscle, the second internal abdominal oblique muscle and the second transversus abdominis muscle is calculated, and the first external abdominal oblique muscle thickness, the first internal abdominal oblique muscle thickness, the first transversus abdominis muscle thickness, the second external abdominal oblique muscle thickness, the second internal abdominal oblique muscle thickness and the second transversus abdominis muscle thickness is obtained;

Specifically, the thickness of the first external abdominal oblique muscle, the first internal abdominal oblique muscle and the first transversus abdominis muscle is calculated, and the first external abdominal oblique muscle thickness, the first internal abdominal oblique muscle thickness and the first transversus abdominis muscle thickness is obtained, comprising:

Aline segment corresponding to the first fascia of quiet expiration, the second fascia of quiet expiration, the third fascia of quiet expiration and the fourth fascia of quiet expiration is constructed, and a corresponding line segment is obtained;

The line segment corresponding to the first fascia of quiet expiration, the second fascia of quiet expiration, the third fascia of quiet expiration and the fourth fascia of quiet expiration is split into a plurality of sub-line segments;

The points with the maximum and minimum slope in each sub-line segment, which are corresponding to the first fascia of quiet expiration, the second fascia of quiet expiration, the third fascia of quiet expiration and the fourth fascia of quiet expiration are selected as key points;

The key point on the second fascia of quiet expiration, which has the shortest absolute distance from each key point on the first fascia of quiet expiration is selected, and a corresponding first key point pair is formed. The average value of the distance of the first key point pair is calculated, and the first external abdominal oblique muscle thickness is obtained;

The key point on the third fascia of quiet expiration, which has the shortest absolute distance from each key point on the second fascia of quiet expiration is selected, and a corresponding second key point pair is formed. The average value of the distance of the second key point pair is calculated, and the first internal oblique muscle thickness is obtained;

The key point on the fourth fascia of quiet expiration, which has the shortest absolute distance from each key point on the third fascia of quiet expiration is selected, and a corresponding third key point pair is formed. The average value of the distance of the third key point pair is calculated, and the first transversus abdominis muscle thickness is obtained.

Figure 3:
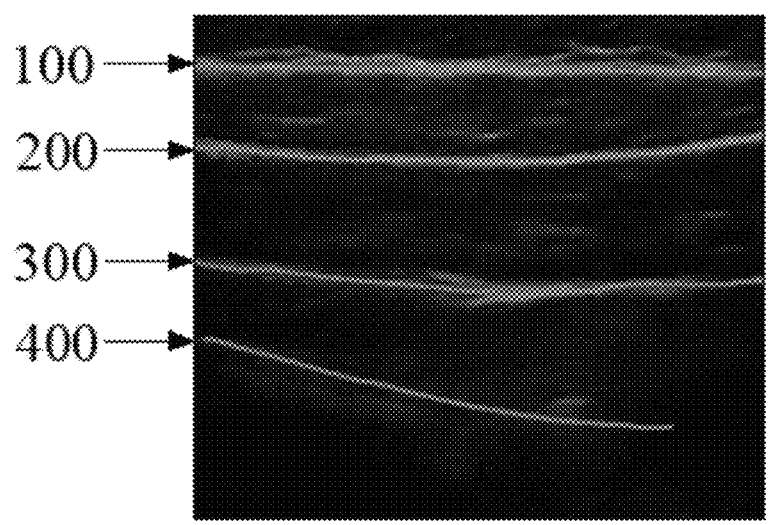
FIG. 3 is a diagram illustrating a line segment corresponding to a first abdominal ultrasound image of user at the end of quiet expiration provided by the present invention.

In practical application, after obtaining the first connected region, the second connected region, the third connected region and the fourth connected region, which are corresponding to the first fascia of quiet expiration, the second fascia of quiet expiration, the third fascia of quiet expiration and the fourth fascia of quiet expiration, then the curve fitting model in the prior art is utilized to fit each pixel in the first connected region, the second connected region, the third connected region and the fourth connected region. As shown in FIG. 3, the line segment corresponding to the first fascia of quiet expiration, the second fascia of quiet expiration, the third fascia of quiet expiration, and the fourth fascia of quiet expiration is obtained. The direction of each line segment is determined according to the starting point and end point of each line segment. According to the number of the preset sub-line segment, an average segmentation is performed on the line segment in the direction of each line segment, and corresponding a plurality of sub-line segments are obtained. The number of preset sub-line segment is set according to the actual situation. The more the number of preset sub-line segment, the higher the measurement accuracy.

Figure 4:
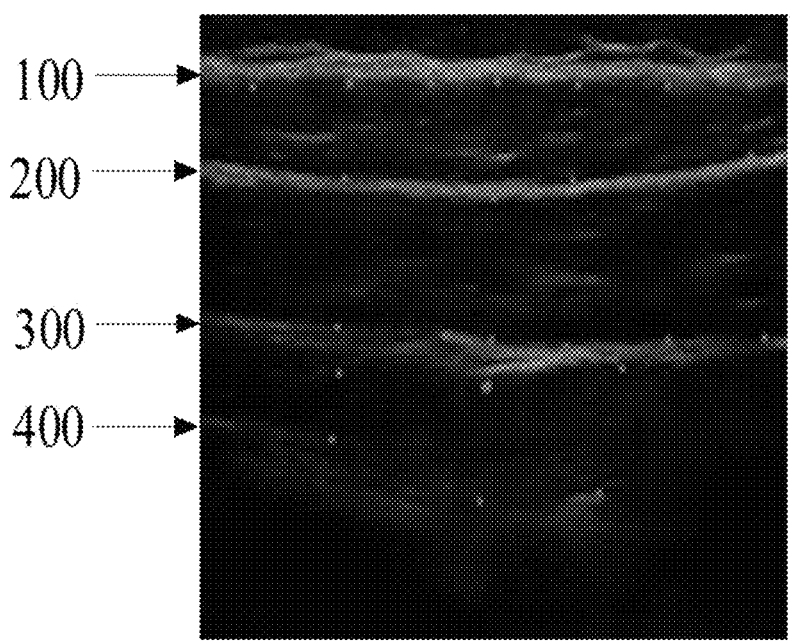
FIG. 4 is a diagram illustrating a key point corresponding to a first abdominal ultrasound image of user at the end of quiet expiration provided by the present invention.

In the present embodiment, as shown in FIG. 4, the points with the largest and smallest slope in each sub-line segment corresponding to the first fascia of quiet expiration are selected as key points, and all key points corresponding to the first fascia of quiet expiration are obtained. The same method as the first fascia of quiet expiration is used, and all key points corresponding to the second fascia of quiet expiration, all key points corresponding to the third fascia of quiet expiration and all key points corresponding to the fourth fascia of quiet expiration are obtained, in order to obtain all first key point pairs, all second key pairs and all third key point pairs subsequently. The Euclidean distances between the key points corresponding to all first key point pairs, the Euclidean distances between the key points corresponding to all second key point pairs and the Euclidean distances between the key points corresponding to all third key point pairs are calculated. And the average value of the Euclidean distances of all first key point pairs are calculated, and the first external abdominal oblique muscle thickness are obtained; the average value of the Euclidean distances of all second key point pairs are calculated, and the first internal abdominal oblique muscle thickness is obtained; the average value of the Euclidean distances of all third key point pairs are calculated, and the first transversus abdominis muscle thickness is obtained; which helps to smooth out local fluctuations. In the present invention, the method of local averaging (Local Averaging) is used to smooth the data to reduce mutation or unnecessary detail and make the data more readable.

Specifically, the thickness of the second external abdominal oblique muscle, the second internal abdominal oblique muscle and the second transversus abdominis muscle is calculated, and the second external abdominal oblique muscle thickness, the second internal abdominal oblique muscle thickness and the second transversus abdominis muscle thickness is obtained, comprising:

Aline segment model corresponding to the first fascia of abdominal respiration, the second fascia of abdominal respiration, the third fascia of abdominal respiration and the fourth fascia of abdominal respiration is constructed, and a corresponding line segment is obtained;

The line segment corresponding to the first fascia of abdominal respiration, the second fascia of abdominal respiration, the third fascia of abdominal respiration and the fourth fascia of abdominal respiration is split into a plurality of sub-line segments;

The points with the maximum and minimum slope in each of the sub-line segment, which are corresponding to the first fascia of abdominal respiration, the second fascia of abdominal respiration, the third fascia of abdominal respiration and the fourth fascia of abdominal respiration are selected as key points;

The key point on the second fascia of abdominal respiration, which has the shortest absolute distance from each key point on the first fascia of abdominal respiration is selected, and a corresponding fourth key point pair is formed. The average value of the distance of the fourth key point pair is calculated, and the second external abdominal oblique muscle thickness is obtained;

The key point on the third fascia of abdominal respiration, which has the shortest absolute distance from each key point on the second fascia of abdominal respiration is selected, and a corresponding fifth key point pair is formed. The average value of the distance of the fifth key point pair is calculated, and the second internal oblique muscle thickness is obtained;

The key point on the fourth fascia of abdominal respiration, which has the shortest absolute distance from each key point on the third fascia of abdominal respiration is selected, and a corresponding sixth key point pair is formed. The average value of the distance of the sixth key point pair is calculated, and the second transversus abdominis muscle thickness is obtained.

Figure 6:
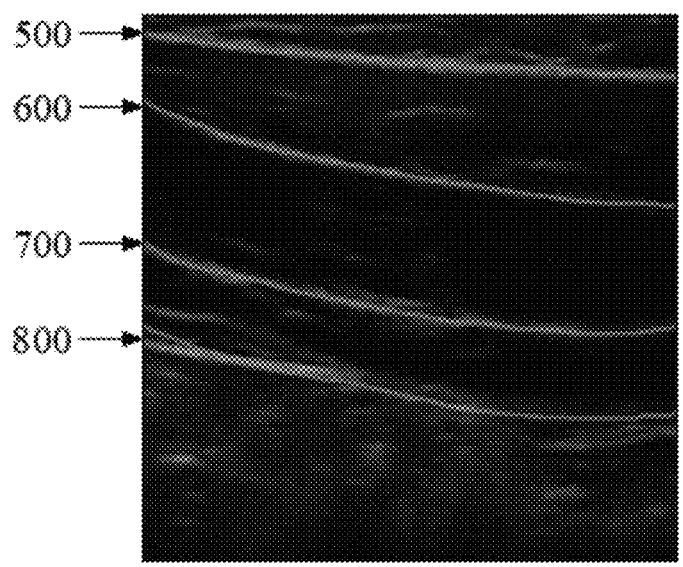
FIG. 6 is a diagram illustrating a line segment corresponding to a second abdominal ultrasound image of user during abdominal expiration provided by the present invention.

In practical application, after obtaining the fifth connected region, the sixth connected region, the seventh connected region and the eighth connected region, which are corresponding to the first fascia of abdominal respiration, the second fascia of abdominal respiration, the third fascia of abdominal respiration and the fourth fascia of abdominal respiration, then the curve fitting model in the prior art is utilized to fit each pixel in the fifth connected region, the sixth connected region, the seventh connected region and the eighth connected region. As shown in FIG. 6, the line segment corresponding to the first fascia of abdominal respiration, the second fascia of abdominal respiration, the third fascia of abdominal respiration and the fourth fascia of abdominal respiration is obtained; the direction of each line segment is determined according to the starting point and end point of each line segment. According to the number of the preset sub-line segment, an average segmentation is performed on the line segment in the direction of each line segment, and corresponding a plurality of sub-line segments are obtained. The number of preset sub-line segment is set according to the actual situation. The more the number of preset sub-line segment, the higher the measurement accuracy.

Figure 7:
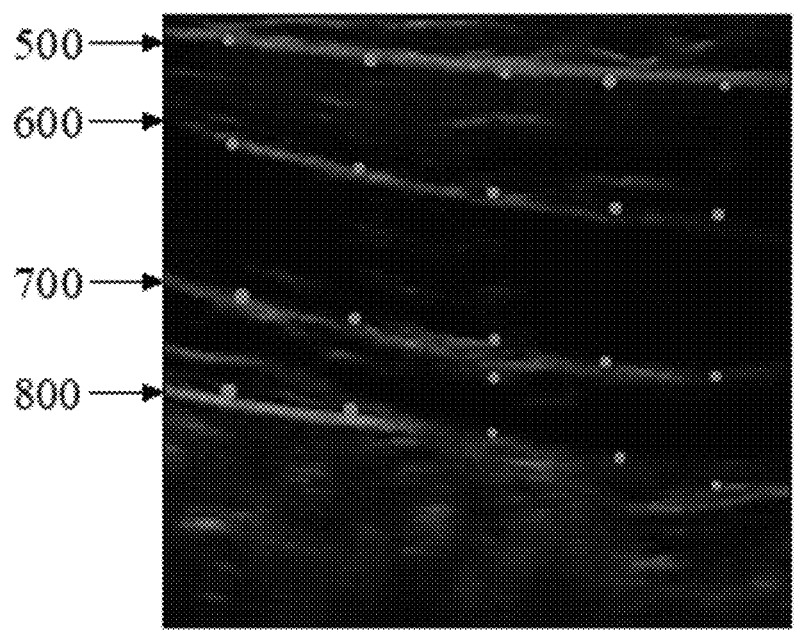
FIG. 7 is a diagram illustrating a key point corresponding to a second abdominal ultrasound image of user during abdominal expiration provided by the present invention.
Figure 8:
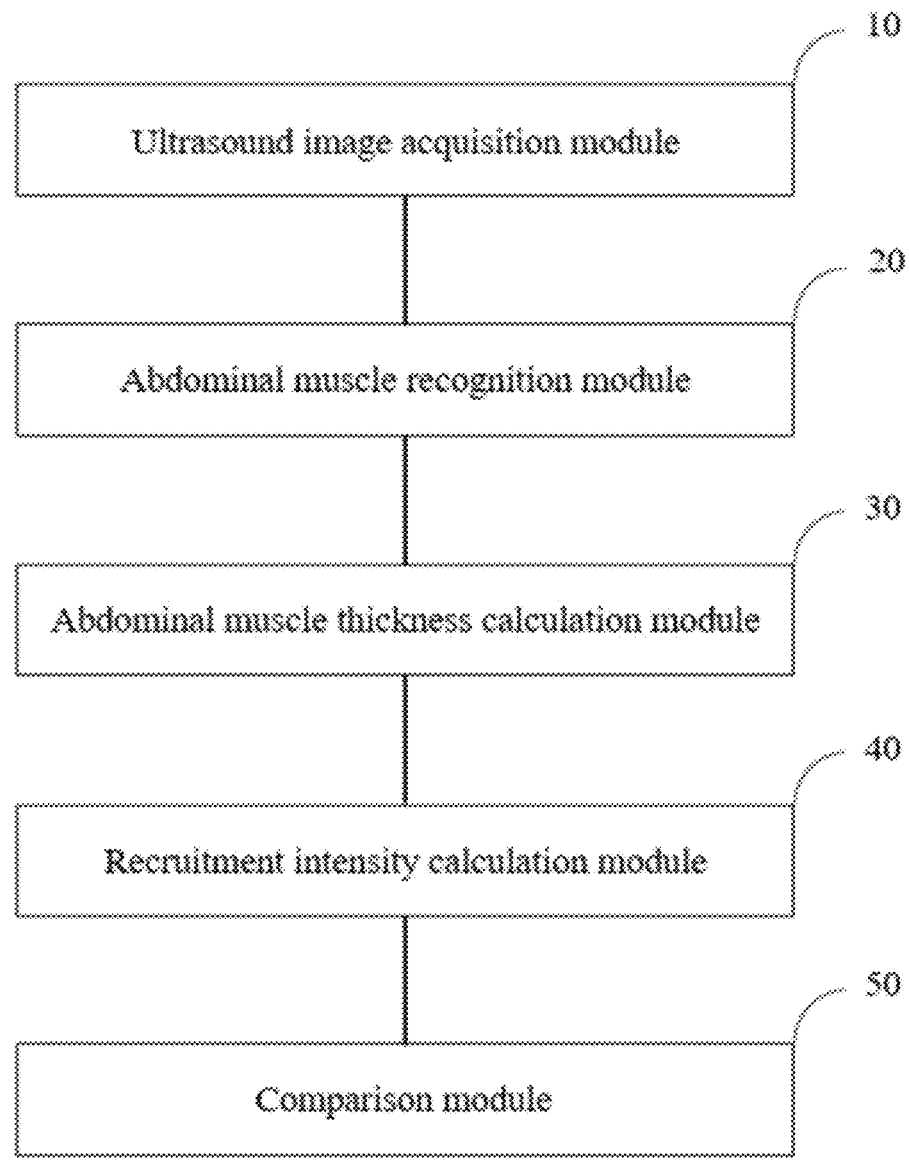
FIG. 8 is a structural diagram illustrating a system for monitoring abdominal respiration based on ultrasound image provided by the present invention.
Figure 9:
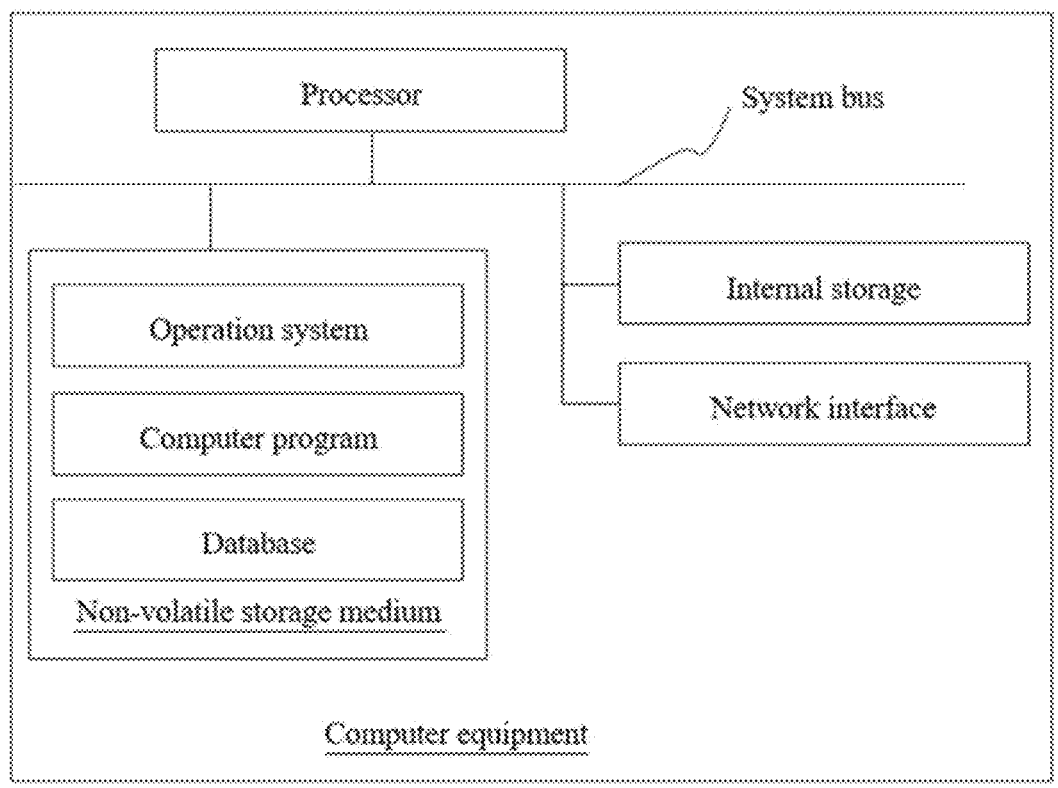
FIG. 9 is an internal structure diagram illustrating a computer equipment provided by embodiments of the present invention.

In the present embodiment, the points with the largest and smallest slope in each sub-line segment, which are corresponding to the first fascia of abdominal respiration are selected as key points, and all key points corresponding to the first fascia of abdominal respiration are obtained. As shown in FIG. 7, the same method as the first fascia of abdominal respiration is used, and all key points corresponding to the second fascia of abdominal respiration, all key points corresponding to the third fascia of abdominal respiration and all key points corresponding to the fourth fascia of abdominal respiration are obtained, in order to obtain all fourth key point pairs, all fifth key pairs and all sixth key point pairs subsequently. The Euclidean distances between the key points corresponding to all fourth key point pairs, the Euclidean distances between the key points corresponding to all fifth key point pairs and the Euclidean distances between the key points corresponding to all sixth key point pairs are calculated. And the average value of the Euclidean distances of all fourth key point pairs are calculated, and the second external abdominal oblique muscle thickness is obtained; the average value of the Euclidean distances of all fifth key point pairs are calculated, and the second internal abdominal oblique muscle thickness is obtained; the average value of the Euclidean distances of all sixth key point pairs are calculated, and the second transversus abdominis muscle thickness is obtained; which helps to smooth out local fluctuations.

Step 4: the external abdominal oblique muscle recruitment intensity is calculated according to the first external abdominal oblique muscle thickness and the second external abdominal oblique muscle thickness; the internal abdominal oblique muscle recruitment intensity is calculated according to the first internal abdominal oblique muscle thickness and the second internal abdominal oblique muscle thickness; the transversus abdominis muscle recruitment intensity is calculated according to the first transversus abdominis muscle thickness and the second transversus abdominis muscle thickness.

Specifically, the external abdominal oblique muscle recruitment intensity is calculated according to the first external abdominal oblique muscle thickness and the second external abdominal oblique muscle thickness; the internal abdominal oblique muscle recruitment intensity is calculated according to the first internal abdominal oblique muscle thickness and the second internal abdominal oblique muscle thickness; the transversus abdominis muscle recruitment intensity is calculated according to the first transversus abdominis muscle thickness and the second transversus abdominis muscle thickness, comprising:

The external abdominal oblique muscle recruitment intensity, the internal abdominal oblique muscle recruitment intensity and the transversus abdominis muscle recruitment intensity is calculated by adopting the recruitment intensity calculation formula, wherein the recruitment intensity calculation formula is as follows:

$$Q = \frac{h_2 - h_1}{h_1},$$

Wherein the Q denotes the recruitment intensity, the $h_2$ denotes the muscle thickness at the end of abdominal respiration and the $h_1$ denotes the muscle thickness at the end of quiet expiration;

The first external abdominal oblique muscle thickness is taken as $h_1$ and the second external abdominal oblique muscle thickness is taken as $h_2$; the $h_1$ and the $h_2$ is substituted into the recruitment intensity calculation formula, and the external abdominal oblique muscle recruitment intensity is obtained. The first internal abdominal oblique muscle thickness is taken as $h_1$ and the second internal abdominal oblique muscle thickness is taken as $h_2$; the $h_1$ and the $h_2$ is substituted into the recruitment intensity calculation formula, and the internal abdominal oblique muscle recruitment intensity is obtained. The first transversus abdominis muscle thickness is taken as $h_1$ and the second transversus abdominis muscle thickness is taken as $h_2$; the $h_1$ and the $h_2$ is substituted into the recruitment intensity calculation formula, and the transversus abdominis muscle recruitment intensity is obtained.

In practical application, the external abdominal oblique muscle recruitment intensity, the internal abdominal oblique muscle recruitment intensity and the transversus abdominis muscle recruitment intensity during user's abdominal respiration is calculated according to the recruitment intensity calculation formula. Through the method, the thickness of transversus abdominis muscle, internal abdominal oblique muscle and external abdominal oblique muscle during user's abdominal respiration can be measured in real time, and the corresponding recruitment intensity is calculated, and the external abdominal oblique muscle recruitment intensity, the internal abdominal oblique muscle recruitment intensity and the transversus abdominis muscle recruitment intensity is converted into histogram; and the histogram height can be changed in real time according to the activity of the abdominal muscle, which can provide visual feedback to user.

Step 5: the external abdominal oblique muscle recruitment intensity, the internal abdominal oblique muscle recruitment intensity and the transversus abdominis muscle recruitment intensity, which are corresponding to each of the second abdominal ultrasound image is compared with a corresponding preset target value, and a monitoring result is obtained.

In practical application, a preset target value comprises: a preset external abdominal oblique muscle target value, a preset internal abdominal oblique muscle target value and a preset transversus abdominis muscle target value. The preset external abdominal oblique muscle target value, the preset internal abdominal oblique muscle target value and the preset transversus abdominis muscle target value can be a reference value of external abdominal oblique muscle recruitment intensity, a reference value of the internal abdominal oblique muscle recruitment strength and a reference value of the transversus abdominis muscle recruitment strength given by doctor according to user's own physical condition. A preset target value is input by user in advance. The external abdominal oblique muscle recruitment intensity, the internal abdominal oblique muscle recruitment intensity and the transversus abdominis muscle recruitment intensity, which are corresponding to each of the second abdominal ultrasound image, is compared with the preset target value. When the external abdominal oblique muscle recruitment intensity, the internal abdominal oblique muscle recruitment intensity and transversus abdominis muscle recruitment intensity reaches the corresponding preset target value, user's abdominal respiration is judged to be correct. So that the monitoring of user's abdominal respiration process is realized, and the training quality is improved. Doctor can also provide respiratory training guidance or change the respiratory training prescription according to the measured external abdominal oblique muscle recruitment strength, internal abdominal oblique muscle recruitment strength and transversus abdominis muscle recruitment strength, which ensures the effectiveness of abdominal respiratory training.

A method for monitoring abdominal respiration based on ultrasound image in the present invention, realizes a monitoring of abdominal respiration in real time. The abdominal muscle thickness and the recruitment intensity is calculated; and the recruitment intensity is compared with the preset target value, and a monitoring result is obtained. So that user can self-monitor the training of abdominal respiration and meet user's home-based rehabilitation needs.

As shown in FIG. 4, the embodiment of the present invention also provides a system for monitoring abdominal respiration based on ultrasound image, comprising:

An ultrasound image acquisition module 10 is used for acquiring user's first abdominal ultrasound image at the calm end of expiration and a plurality of second abdominal ultrasound images in the condition of abdominal respiration;

An abdominal muscle recognition module 20 is used for performing image recognition on the first abdominal ultrasound image, and the first external abdominal oblique muscle, the first internal abdominal oblique muscle and the first transversus abdominis muscle is recognized. Image recognition is performed on each of the second abdominal ultrasound image, and the second external abdominal oblique muscle, the second internal abdominal oblique muscle and the second transversus abdominis muscle is recognized;

An abdominal muscle thickness calculation module 30 is used for calculating the thicknesses of the first external abdominal oblique muscle, the first internal abdominal oblique muscle, the first transversus abdominis muscle, the second external abdominal oblique muscle, the second internal abdominal oblique muscle and the second transversus abdominis muscle, and the first external abdominal oblique muscle thickness, the first internal abdominal oblique muscle thickness, the first transversus abdominis muscle thickness, the second external abdominal oblique muscle thickness, the second internal abdominal oblique muscle thickness and the second transversus abdominis muscle thickness is obtained;

A recruitment intensity calculation module 40 is used for calculating external abdominal oblique muscle recruitment intensity according to the first external abdominal oblique muscle thickness and the second external abdominal oblique muscle thickness; the internal abdominal oblique muscle recruitment intensity is calculated according to the first internal abdominal oblique muscle thickness and the second internal abdominal oblique muscle thickness; the transversus abdominis muscle recruitment intensity is calculated according to the first transversus abdominis muscle thickness and the second transversus abdominis muscle thickness;

A comparison module 50 is used for comparing the external abdominal oblique muscle recruitment intensity, the internal abdominal oblique muscle recruitment intensity and the transversus abdominis muscle recruitment intensity corresponding to each of the second abdominal ultrasound image with the corresponding preset target value, and a monitoring result is obtained.

In one embodiment, the abdominal muscle recognition module, comprising:

A preprocessing unit is used for preprocessing the first abdominal ultrasound image, and a first preprocessing image is obtained;

A recognition unit is used for recognizing the first fascia of quiet expiration, the second fascia of quiet expiration, the third fascia of quiet expiration and the fourth fascia of quiet expiration which are sequentially arranged according to the pixel values of the first preprocessed image. The abdominal muscle between the first fascia of quiet expiration and the second fascia of quiet expiration is the first external abdominal oblique muscle; the abdominal muscle between the second fascia of quiet expiration and the third fascia of quiet expiration is the first internal abdominal oblique muscle; the abdominal muscle between the third fascia of the quiet expiration and the fourth fascia of the quiet expiration is the first transversus abdominis muscle.

For the specific composition of the abdominal respiration monitoring system based on ultrasound image, please refer to the composition of the abdominal respiration monitoring method based on ultrasound image above, which will not be repeated herein. The individual module of the abdominal respiration monitoring system based on ultrasound images described above can be implemented in whole or in part through software, hardware, and a combination thereof. The above each module can be embedded in or independent of the processor in the computer equipment in the form of hardware, or can be stored in the memory in the computer equipment in the form of software, so that the processor can call and perform the corresponding operations of the above each module.

In one embodiment, a computer equipment is provided, which can be a server, and its internal structure diagram can be shown in FIG. 5. The computer equipment includes processor, memory, network interface and database, which are connected via a system bus. Wherein, the processor of this computer equipment is used to provide computing and control capability. The memory of the computer device includes a non-volatile storage medium and internal memory. This non-volatile storage medium stores the operating system, computer program and database. This internal memory provides the environment for the operation of operating systems and computer programs in non-volatile storage media. The network interface of this computer equipment is used to communicate with external terminal through network connection. This computer program is executed by the processor to implement a method for monitoring abdominal respiration based on ultrasound image.

A person skilled in the art can understand that the structure shown in FIG. 5 is merely a block diagram of a partial structure related to the solution of the present application, and does not constitute a limitation on a computer equipment applied to the solution of the present application. The specific computer equipment can include more or fewer components than those shown in the drawings, or combine some components, or have different component layouts.

In one embodiment, a computer equipment is provided, comprising a memory and a processor. The memory stores a computer program; the processor implements the following steps when executing the computer program:

A first abdominal ultrasound image of user at the end of quiet expiration and a plurality of second abdominal ultrasound images under abdominal respiration condition is acquired;

Image recognition is performed on the first abdominal ultrasound image, and the first external abdominal oblique muscle, the first internal abdominal oblique muscle and the first transversus abdominis muscle is recognized. Image recognition is performed on each of the second abdominal ultrasound image, and the second external abdominal oblique muscle, the second internal abdominal oblique muscle and the second transversus abdominis muscle is recognized;

The thickness of the first external abdominal oblique muscle, the first internal abdominal oblique muscle, the first transversus abdominis muscle, the second external abdominal oblique muscle, the second internal abdominal oblique muscle and the second transversus abdominis muscle is calculated, and the first external abdominal oblique muscle thickness, the first internal abdominal oblique muscle thickness, the first transversus abdominis muscle thickness, the second external abdominal oblique muscle thickness, the second internal abdominal oblique muscle thickness and the second transversus abdominis muscle thickness is obtained;

The external abdominal oblique muscle recruitment intensity is calculated according to the first external oblique muscle thickness and the second external abdominal oblique muscle thickness; the internal abdominal oblique muscle recruitment intensity is calculated according to the first internal abdominal oblique muscle thickness and the second internal abdominal oblique muscle thickness; the transversus abdominis muscle recruitment intensity is calculated according to the first transversus abdominis muscle thickness and the second transversus abdominis muscle thickness;

The external abdominal oblique muscle recruitment intensity, the internal abdominal oblique muscle recruitment intensity and the transversus abdominis muscle recruitment intensity corresponding to each mentioned second abdominal ultrasound image is compared with a corresponding preset target value, and a monitoring result is obtained.

In one embodiment, image recognition is performed on the first abdominal ultrasound image, and the first external abdominal oblique muscle, the first internal abdominal oblique muscle and the first transversus abdominis muscle is recognized, comprising:

The first abdominal ultrasound image is preprocessed, and a first preprocessed image is obtained;

According to the pixel value of the first preprocessed image, the first fascia of quiet expiration, the second fascia of quiet expiration, the third fascia of quiet expiration and the fourth fascia of quiet expiration which are sequentially arranged is recognized. The abdominal muscle between the first fascia of quiet expiration and the second fascia of quiet expiration is the first external abdominal oblique muscle; the abdominal muscle between the second fascia of quiet expiration and the third fascia of quiet expiration is the first internal abdominal oblique muscle; the abdominal muscle between the third fascia of quiet expiration and the fourth fascia of quiet expiration is the first transversus abdominis muscle.

In one embodiment, the thickness of the first external abdominal oblique muscle, the first internal abdominal oblique muscle and the first transversus abdominis muscle is calculated, and the first external abdominal oblique muscle thickness, the first internal abdominal oblique muscle thickness and the first transversus abdominis muscle thickness is obtained, comprising:

Aline segment corresponding to the first fascia of quiet expiration, the second fascia of quiet expiration, the third fascia of quiet expiration and the fourth fascia of quiet expiration is constructed;

The line segment corresponding to the first fascia of quiet expiration, the second fascia of quiet expiration, the third fascia of quiet expiration and the fourth fascia of quiet expiration is split into a plurality of sub-line segments;

The points with the maximum and minimum slope in each of the sub-line segment, which are corresponding to the first fascia of quiet expiration, the second fascia of quiet expiration, the third fascia of quiet expiration and the fourth fascia of quiet expiration are selected as key points;

The key point on the second fascia of quiet expiration, which has the shortest absolute distance from each key point on the first fascia of quiet expiration is selected, and a corresponding first key point pair is formed. The average value of the distance of the first key point pair is calculated, and the first external abdominal oblique muscle thickness is obtained;

The key point on the third fascia of quiet expiration, which has the shortest absolute distance from each key point on the second fascia of quiet expiration is selected, and a corresponding second key point pair is formed. The average value of the distance of the second key point pair is calculated, and the first internal abdominal oblique muscle thickness is obtained;

The key point on the fourth fascia of quiet expiration, which has the shortest absolute distance from each key point on the third fascia of quiet expiration is selected, and a corresponding third key point pair is formed. The average value of the distance of the third key point pair is calculated, and the first transversus abdominis muscle thickness is obtained.

In one embodiment, image recognition is performed on each of the second abdominal ultrasound image, and the second external abdominal oblique muscle, the second internal abdominal oblique muscle and the second transversus abdominis muscle is recognized, comprising:

The second abdominal ultrasound image is preprocessed, and a second preprocessed image is obtained;

According to the pixel value of the second preprocessed image, a first fascia of abdominal respiration, the second fascia of abdominal respiration, the third fascia of abdominal respiration and the fourth fascia of abdominal respiration which are sequentially arranged is recognized. The abdominal muscle between the first fascia of abdominal respiration and the second fascia of abdominal respiration is the second external abdominal oblique muscle; the abdominal muscle between the second fascia of abdominal respiration and the third fascia of abdominal respiration is the second internal abdominal oblique muscle; the abdominal muscle between the third fascia of abdominal respiration and the fourth fascia of abdominal respiration is the second transversus abdominis muscle.

In one embodiment, the thickness of the second external abdominal oblique muscle, the second internal abdominal oblique muscle and the second transversus abdominis muscle is calculated, and the second external abdominal oblique muscle thickness, the second internal abdominal oblique muscle thickness and the second transversus abdominis muscle thickness is obtained, comprising:

Aline segment model corresponding to the first fascia of abdominal respiration, the second fascia of abdominal respiration, the third fascia of abdominal respiration and the fourth fascia of abdominal respiration is constructed, and a corresponding line segment is obtained;

The line segment corresponding to the first fascia of abdominal respiration, the second fascia of abdominal respiration, the third fascia of abdominal respiration and the fourth fascia of abdominal respiration is split into a plurality of sub-line segments;

The points with the maximum and minimum slope in each of the sub-line segment, which are corresponding to the first fascia of abdominal respiration, the second fascia of abdominal respiration, the third fascia of abdominal respiration and the fourth fascia of abdominal respiration are selected as key points;

The key point on the second fascia of abdominal respiration, which has the shortest absolute distance from each key point on the first fascia of abdominal respiration is selected, and a corresponding fourth key point pair is formed. The average value of the distance of the fourth key point pair is calculated, and the second external abdominal oblique muscle thickness is obtained;

The key point on the third fascia of abdominal respiration, which has the shortest absolute distance from each key point on the second fascia of abdominal respiration is selected, and a corresponding fifth key point pair is formed. The average value of the distance of the fifth key point pair is calculated, and the second internal abdominal oblique muscle thickness is obtained;

The key point on the fourth fascia of abdominal respiration, which has the shortest absolute distance from each key point on the third fascia of abdominal respiration is selected, and a corresponding sixth key point pair is formed. The average value of the distance of the sixth key point pair is calculated, and the second transversus abdominis muscle thickness is obtained.

In one embodiment, the external abdominal oblique muscle recruitment intensity is calculated according to the first external abdominal oblique muscle thickness and the second external abdominal oblique muscle thickness; the internal abdominal oblique muscle recruitment intensity is calculated according to the first internal abdominal oblique muscle thickness and the second internal abdominal oblique muscle thickness; the transversus abdominis muscle recruitment intensity is calculated according to the first transversus abdominis muscle thickness and the second transversus abdominis muscle thickness, comprising:

The external abdominal oblique muscle recruitment intensity, the internal abdominal oblique muscle recruitment intensity and the transversus abdominis muscle recruitment intensity is calculated by adopting the recruitment intensity calculation formula, wherein the recruitment intensity calculation formula is as follows:

$$Q = \frac{h_2 - h_1}{h_1},$$

Wherein the Q denotes the recruitment intensity, the $h_2$ denotes the muscle thickness at the end of abdominal respiration and the $h_1$ denotes the muscle thickness at the end of quiet expiration;

The first external abdominal oblique muscle thickness is taken as $h_1$ and the second external abdominal oblique muscle thickness is taken as $h_2$; the h1 and the h2 is substituted into the recruitment intensity calculation formula, and the external abdominal oblique muscle recruitment intensity is obtained. The first internal abdominal oblique muscle thickness is taken as $h_1$ and the second internal abdominal oblique muscle thickness is taken as $h_2$; the h1 and the h2 is substituted into the recruitment intensity calculation formula, and the internal abdominal oblique muscle recruitment intensity is obtained. The first transversus abdominis muscle thickness is taken as $h_1$ and the second transversus abdominis muscle thickness is taken as $h_2$; the h1 and the h2 is substituted into the recruitment intensity calculation formula, and the transversus abdominis muscle recruitment intensity is obtained.

In one embodiment, a computer-readable storage medium is provided, on which a computer program is stored. When the computer program is executed by a processor, the following steps are implemented.

A first abdominal ultrasound image of user at the end of quiet expiration and a plurality of second abdominal ultrasound images under abdominal respiration condition is acquired;

Image recognition is performed on the first abdominal ultrasound image, and the first external abdominal oblique muscle, the first internal abdominal oblique muscle and the first transversus abdominis muscle is recognized. Image recognition is performed on each of the second abdominal ultrasound image, and the second external abdominal oblique muscle, the second internal abdominal oblique muscle and the second transversus abdominis muscle is recognized;

The thickness of the first external abdominal oblique muscle, the first internal abdominal oblique muscle, the first transversus abdominis muscle, the second external abdominal oblique muscle, the second internal abdominal oblique muscle and the second transversus abdominis muscle is calculated, and the first external abdominal oblique muscle thickness, the first internal abdominal oblique muscle thickness, the first transversus abdominis muscle thickness, the second external abdominal oblique muscle thickness, the second internal abdominal oblique muscle thickness and the second transversus abdominis muscle thickness is obtained;

The external abdominal oblique muscle recruitment intensity is calculated according to the first external oblique muscle thickness and the second external abdominal oblique muscle thickness; the internal abdominal oblique muscle recruitment intensity is calculated according to the first internal abdominal oblique muscle thickness and the second internal abdominal oblique muscle thickness; the transversus abdominis muscle recruitment intensity is calculated according to the first transversus abdominis muscle thickness and the second transversus abdominis muscle thickness;

The external abdominal oblique muscle recruitment intensity, the internal abdominal oblique muscle recruitment intensity and the transversus abdominis muscle recruitment intensity corresponding to each of the second abdominal ultrasound image is compared with a corresponding preset target value, and a monitoring result is obtained.

In one embodiment, image recognition is performed on the first abdominal ultrasound image, and the first external abdominal oblique muscle, the first internal abdominal oblique muscle and the first transversus abdominis muscle is recognized, comprising:

The first abdominal ultrasound image is preprocessed, and a first preprocessed image is obtained;

According to the pixel value of the first preprocessed image, the first fascia of quiet expiration, the second fascia of quiet expiration, the third fascia of quiet expiration and the fourth fascia of quiet expiration which are sequentially arranged is recognized. The abdominal muscle between the first fascia of quiet expiration and the second fascia of quiet expiration is the first external abdominal oblique muscle; the abdominal muscle between the second fascia of quiet expiration and the third fascia of quiet expiration is the first internal abdominal oblique muscle; the abdominal muscle between the third fascia of quiet expiration and the fourth fascia of quiet expiration is the first transversus abdominis muscle.

In one embodiment, the thickness of the first external abdominal oblique muscle, the first internal abdominal oblique muscle and the first transversus abdominis muscle is calculated, and the first external abdominal oblique muscle thickness, the first internal abdominal oblique muscle thickness and the first transversus abdominis muscle thickness is obtained, comprising:

Aline segment corresponding to the first fascia of quiet expiration, the second fascia of quiet expiration, the third fascia of quiet expiration and the fourth fascia of quiet expiration is constructed;

The line segment corresponding to the first fascia of quiet expiration, the second fascia of quiet expiration, the third fascia of quiet expiration and the fourth fascia of quiet expiration is split into a plurality of sub-line segments;

The points with the maximum and minimum slopes in each sub-line segment, which are corresponding to the first fascia of quiet expiration, the second fascia of quiet expiration, the third fascia of quiet expiration and the fourth fascia of quiet expiration are selected as key points;

The key point on the second fascia of quiet expiration, which has the shortest absolute distance from each key point on the first fascia of quiet expiration is selected, and a corresponding first key point pair is formed. The average value of the distance of the first key point pair is calculated, and the first external abdominal oblique muscle thickness is obtained;

The key point on the third fascia of quiet expiration, which has the shortest absolute distance from each key point on the second fascia of quiet expiration is selected, and a corresponding second key point pair is formed. The average value of the distance of the second key point pair is calculated, and the first internal oblique muscle thickness is obtained;

The key point on the fourth fascia of quiet expiration, which has the shortest absolute distance from each key point on the third fascia of quiet expiration is selected, and a corresponding third key point pair is formed. The average value of the distance of the third key point pair is calculated, and the first transversus abdominis muscle thickness is obtained.

In one embodiment, image recognition is performed on each of the second abdominal ultrasound image, and the second external abdominal oblique muscle, the second internal abdominal oblique muscle and the second transversus abdominis muscle is recognized, comprising:

The second abdominal ultrasound image is preprocessed, and a second preprocessed image is obtained;

According to the pixel value of the second preprocessed image, the first fascia of abdominal respiration, the second fascia of abdominal respiration, the third fascia of abdominal respiration and the fourth fascia of abdominal respiration which are sequentially arranged is recognized. The abdominal muscle between the first fascia of abdominal respiration and the second fascia of abdominal respiration is the second external abdominal oblique muscle; the abdominal muscle between the second fascia of abdominal respiration and the third fascia of abdominal respiration is the second internal abdominal oblique muscle; the abdominal muscle between the third fascia of abdominal respiration and the fourth fascia of abdominal respiration is the second transversus abdominis muscle.

In one embodiment, the thickness of the second external abdominal oblique muscle, the second internal abdominal oblique muscle and the second transversus abdominis muscle is calculated, and the second external abdominal oblique muscle thickness, the second internal abdominal oblique muscle thickness and the second transversus abdominis muscle thickness is obtained, comprising:

Aline segment corresponding to the first fascia of quiet expiration, the second fascia of quiet expiration, the third fascia of quiet expiration and the fourth fascia of quiet expiration is constructed, and a corresponding line segment is obtained;

The line segment corresponding to the first fascia of quiet expiration, the second fascia of quiet expiration, the third fascia of quiet expiration and the fourth fascia of quiet expiration is split into a plurality of sub-line segments;

The points with the maximum and minimum slope in each of the sub-line segment, which are corresponding to the first fascia of quiet expiration, the second fascia of quiet expiration, the third fascia of quiet expiration and the fourth fascia of quiet expiration are selected as key points;

The key point on the second fascia of abdominal respiration, which has the shortest absolute distance from each key point on the first fascia of abdominal respiration is selected, and a corresponding fourth key point pair is formed. The average value of the distance of the fourth key point pair is calculated, and the second external abdominal oblique muscle thickness is obtained;

The key point on the third fascia of abdominal respiration, which has the shortest absolute distance from each key point on the second fascia of abdominal respiration is selected, and a corresponding fifth key point pair is formed. The average value of the distance of the fifth key point pair is calculated, and the second internal abdominal oblique muscle thickness is obtained;

The key point on the fourth fascia of abdominal respiration, which has the shortest absolute distance from each key point on the third fascia of abdominal respiration is selected, and a corresponding sixth key point pair is formed. The average value of the distance of the sixth key point pair is calculated, and the second transversus abdominis muscle thickness is obtained.

In one embodiment, the external abdominal oblique muscle recruitment intensity is calculated according to the first external abdominal oblique muscle thickness and the second external abdominal oblique muscle thickness; the internal abdominal oblique muscle recruitment intensity is calculated according to the first internal abdominal oblique muscle thickness and the second internal abdominal oblique muscle thickness; the transversus abdominis muscle recruitment intensity is calculated according to the first transversus abdominis muscle thickness and the second transversus abdominis muscle thickness, comprising:

The external abdominal oblique muscle recruitment intensity, the internal abdominal oblique muscle recruitment intensity and the transversus abdominis muscle recruitment intensity is calculated by adopting the recruitment intensity calculation formula, wherein the recruitment intensity calculation formula is as follows:

$$Q = \frac{h_2 - h_1}{h_1},$$

Wherein the Q denotes the recruitment intensity, the h2 denotes the muscle thickness at the end of abdominal respiration and the h1 denotes the muscle thickness at the end of quiet expiration;

The first external abdominal oblique muscle thickness is taken as h1 and the second external abdominal oblique muscle thickness is taken as h2; the h1 and the h2 is substituted into the recruitment intensity calculation formula, and the external abdominal oblique muscle recruitment intensity is obtained. The first internal abdominal oblique muscle thickness is taken as h1 and the second internal abdominal oblique muscle thickness is taken as h2; the h1 and the h2 is substituted into the recruitment intensity calculation formula, and the internal abdominal oblique muscle recruitment intensity is obtained. The first transversus abdominis muscle thickness is taken as h1 and the second transversus abdominis muscle thickness is taken as h2; the h1 and the h2 is substituted into the recruitment intensity calculation formula, and the transversus abdominis muscle recruitment intensity is obtained.

An ordinary person skilled in the art can understand that all or part of the processes in the method for realizing the above embodiments can be completed by instructing related hardware through a computer program. The computer program can be stored in a non-volatile computer readable storage medium. When the computer program is executed, the procedures of the embodiments of the above methods can be included. Wherein, any reference to memory, storage, database, or other medium used in each of the embodiment provided in the present application can include non-volatile and/or volatile memory. Non-volatile memory can include read-only memory (ROM), programmable ROM (PROM), electrically programmable ROM (EPROM), electrically erasable programmable ROM (EEPROM), or flash memory. Volatile memory can include random-access memory (RAM) or external cache memory. As an illustration and not a limitation, RAM is available in various forms, such as static RAM (SRAM), dynamic RAM (DRAM), synchronous DRAM (SDRAM), dual data rate SDRAM (DDRSDRAM), enhanced SDRAM (ESDRAM), synchronous link (Synch link) DRAM (SLDRAM), memory bus (Rambus) direct RAM, direct memory bus dynamic RAM (DRDRAM) and memory bus dynamic RAM (RDRAM), etc.

Each of the technical feature in the above embodiments can be arbitrarily combined. For the sake of conciseness of description, not all possible combinations of each of the technical feature in the above embodiments are described. However, as long as there is no contradiction between the combinations of these technical features, they shall be considered to be within the scope of this specification.

What is claimed is:

1. A method for monitoring abdominal respiration based on ultrasound image, comprising:

acquiring a first abdominal ultrasound image at an end of quiet expiration of a user and a plurality of second abdominal ultrasound images under abdominal respiration condition of the user;

recognizing a first external abdominal oblique muscle, a first internal abdominal oblique muscle and a first transversus abdominis muscle based on the first abdominal ultrasound image; recognizing a second external abdominal oblique muscle, a second internal abdominal oblique muscle and a second transversus abdominis muscle based on each of the second abdominal ultrasound image;

calculating a thickness of the first external abdominal oblique muscle, the first internal abdominal oblique muscle, the first transversus abdominis muscle, the second external abdominal oblique muscle, the second internal abdominal oblique muscle and the second transversus abdominis muscle to obtain a first external abdominal oblique muscle thickness, a first internal abdominal oblique muscle thickness, a first transversus abdominis muscle thickness, a second external abdominal oblique muscle thickness, a second internal abdominal oblique muscle thickness and a second transversus abdominis muscle thickness;

calculating an external abdominal oblique muscle recruitment intensity according to the first external oblique muscle thickness and the second external abdominal oblique muscle thickness; calculating an internal abdominal oblique muscle recruitment intensity according to the first internal abdominal oblique muscle thickness and the second internal abdominal oblique muscle thickness; calculating a transversus abdominis muscle recruitment intensity according to the first transversus abdominis muscle thickness and the second transversus abdominis muscle thickness;

obtaining a monitoring result by comparing the external abdominal oblique muscle recruitment intensity, the internal abdominal oblique muscle recruitment intensity and the transversus abdominis muscle recruitment intensity with corresponding preset target values;

wherein recognizing the first external abdominal oblique muscle, the first internal abdominal oblique muscle and the first transversus abdominis muscle based on the first abdominal ultrasound image comprises:

obtaining a first preprocessed image by preprocessing the first abdominal ultrasound image;

according to a pixel value of the first preprocessed image, recognizing a first fascia of quiet expiration, a second fascia of quiet expiration, a third fascia of quiet expiration and a fourth fascia of quiet expiration which are sequentially arranged; an abdominal muscle between the first fascia of quiet expiration and the second fascia of quiet expiration being the first external abdominal oblique muscle; an abdominal muscle between the second fascia of quiet expiration and the third fascia of quiet expiration being the first internal abdominal oblique muscle; an abdominal muscle between the third fascia of quiet expiration and the fourth fascia of quiet expiration being the first transversus abdominis muscle;

wherein calculating the thickness of the first external abdominal oblique muscle, the first internal abdominal oblique muscle and the first transversus abdominis muscle to obtain the first external abdominal oblique muscle thickness, the first internal abdominal oblique muscle thickness and the first transversus abdominis muscle thickness is obtained, comprises:

constructing line segments corresponding to the first fascia of quiet expiration, the second fascia of quiet expiration, the third fascia of quiet expiration and the fourth fascia of quiet expiration;

splitting each of the line segments corresponding to the first fascia of quiet expiration, the second fascia of quiet expiration, the third fascia of quiet expiration and the fourth fascia of quiet expiration into a plurality of first sub-line segments;

selecting a points with a maximum slope and a point with a minimum slope in each first sub-line segment as key points;

forming a first key point pair for each key point on the second fascia of quiet expiration, the first key point pair having a key point on the second fascia of quiet expiration and a key point on the first fascia of quiet expiration that has a shortest absolute distance from the key point on the second fascia of quiet expiration; calculating an average value of distance of the first key point pair for each key point on the second fascia of quiet expiration, and the average value of distance of the first key point pair being the first external abdominal oblique muscle thickness;

forming a second key point pair for each key point on the third fascia of quiet expiration, the second key point pair having a key point on the third fascia of quiet expiration and a key point on the second fascia of quiet expiration that has a shortest absolute distance from the key point on the third fascia of quiet expiration; calculating an average value of distance of the second key point pair for each key point on the third fascia of quiet expiration, and the average value of distance of the second key point pair being the first internal abdominal oblique muscle thickness;

forming a third key point pair for each key point on the fourth fascia of quiet expiration, the third key point pair having a key point on the fourth fascia of quiet expiration and a key point on the third fascia of quiet expiration that has a shortest absolute distance from the key point on the fourth fascia of quiet expiration; calculating an average value of distance of the third key point pair for each key point on the fourth fascia of quiet expiration, and the average value of distance of the third key point pair being the first transversus abdominis muscle thickness.

2. The method for monitoring abdominal respiration based on ultrasound image according to claim 1, wherein recognizing the second external abdominal oblique muscle, the second internal abdominal oblique muscle and the second transversus abdominis muscle based on each of the second abdominal ultrasound image comprises:

obtaining a second preprocessed image by preprocessing the second abdominal ultrasound image;

according to a pixel value of the second preprocessed image, recognizing a first fascia of abdominal respiration, a second fascia of abdominal respiration, a third fascia of abdominal respiration and a fourth fascia of abdominal respiration which are sequentially arranged; an abdominal muscle between the first fascia of abdominal respiration and the second fascia of abdominal respiration being the second external abdominal oblique muscle; an abdominal muscle between the second fascia of abdominal respiration and the third fascia of abdominal respiration being the second internal abdominal oblique muscle; an abdominal muscle between the third fascia of abdominal respiration and the fourth fascia of abdominal respiration being the second transversus abdominis muscle.

3. The method for monitoring abdominal respiration based on ultrasound image according to claim 2, wherein calculating the thickness of the second external abdominal oblique muscle, the second internal abdominal oblique muscle and the second transversus abdominis muscle to obtain the second external abdominal oblique muscle thickness, the second internal abdominal oblique muscle thickness and the second transversus abdominis muscle thickness is obtained, comprises:

constructing line segments corresponding to the first fascia of abdominal respiration, the second fascia of abdominal respiration, the third fascia of abdominal respiration and the fourth fascia of abdominal respiration is constructed;

splitting each of the line segments corresponding to the first fascia of abdominal respiration, the second fascia of abdominal respiration, the third fascia of abdominal respiration and the fourth fascia of abdominal respiration into a plurality of second sub-line segments;

selecting a point with a maximum slope and a point with a minimum slope in each second sub-line segment as further key points;

forming a fourth key point pair for each further key point on the second fascia of abdominal respiration, the fourth key point pair having a further key point on the second fascia of abdominal respiration and a further key point on the first fascia of abdominal respiration that has a shortest absolute distance from the further key point on the second fascia of abdominal respiration; calculating an average value of distance of the fourth key point pair for each further key point on the second fascia of abdominal respiration, and the average value of distance of the fourth key point pair being the second external abdominal oblique muscle thickness;

forming a fifth key point pair for each further key point on the third fascia of abdominal respiration, the fifth key point pair having a further key point on the third fascia of abdominal respiration and a further key point on the second fascia of abdominal respiration that has a shortest absolute distance from the further key point on the third fascia of abdominal respiration; calculating an average value of distance of the fifth key point pair for each further key point on the third fascia of abdominal respiration, and the average value of distance of the fifth key point pair being the second internal abdominal oblique muscle thickness;

forming a sixth key point pair for each further key point on the fourth fascia of abdominal respiration, the sixth key point pair having a further key point on the fourth fascia of abdominal respiration and a further key point on the third fascia of abdominal respiration that has a shortest absolute distance from the further key point on the fourth fascia of abdominal respiration; calculating an average value of distance of the sixth key point pair for each further key point on the fourth fascia of abdominal respiration, and the average value of distance of the sixth key point pair being the second transversus abdominis muscle thickness.

4. The method for monitoring abdominal respiration based on ultrasound image according to claim 1, wherein calculating the external abdominal oblique muscle recruitment intensity according to the first external abdominal oblique muscle thickness and the second external abdominal oblique muscle thickness, calculating the internal abdominal oblique muscle thickness according to the first internal abdominal oblique muscle thickness and the second internal abdominal oblique muscle thickness, and calculating the transversus abdominis muscle recruitment intensity according to the first transversus abdominis muscle thickness and the second transversus abdominis muscle thickness, comprises:

calculating the external abdominal oblique muscle recruitment intensity, the internal abdominal oblique muscle recruitment intensity and the transversus abdominis muscle recruitment intensity by adopting a recruitment intensity calculation formula, wherein the recruitment intensity calculation formula is as follows:

$$Q = \frac{h_2 - h_1}{h_1},$$

wherein Q denotes a recruitment intensity, $h_2$ denotes a muscle thickness at an end of abdominal respiration and $h_1$ denotes a muscle thickness at the end of quiet expiration;

taking the first external abdominal oblique muscle thickness as $h_1$ and the second external abdominal oblique muscle thickness as $h_2$ to calculate the external abdominal oblique muscle recruitment intensity; taking the first internal abdominal oblique muscle thickness as $h_1$ and the second internal abdominal oblique muscle thickness as $h_2$ to calculate the internal abdominal oblique muscle recruitment intensity; taking the first transversus abdominis muscle thickness as $h_1$ and the second transversus abdominis muscle thickness as $h_2$ to calculate the transversus abdominis muscle recruitment intensity.

5. A computer equipment, comprising a memory and a processor; wherein the memory stores a computer program, when the processor executes the computer program, the computer equipment performs the method according to claim 1.

6. A non-transitory computer-readable storage medium, storing a computer program thereon, which when executed by a processor, performs the method according to claim 1.

* * * * *